United States Patent [19]

Georgiev et al.

[11] Patent Number: 4,549,014

[45] Date of Patent: Oct. 22, 1985

[54] ADAMANTYL CONTAINING 1,4-OXAZINONE DERIVATIVES

[75] Inventors: Vassil S. Georgiev, Rochester; George B. Mullen, Avon, both of N.Y.

[73] Assignee: Pennwalt Corporation, Philadelphia, Pa.

[21] Appl. No.: 647,787

[22] Filed: Sep. 6, 1984

[51] Int. Cl.$^4$ ............................................. C07D 265/34
[52] U.S. Cl. ....................................... 544/71; 544/171
[58] Field of Search .................................. 544/71, 171

[56] References Cited

U.S. PATENT DOCUMENTS 3,509,140  4/1970  Roberts et al. ...................... 544/71

Primary Examiner—Robert W. Ramsuer

[57] ABSTRACT

Antimicrobial or anti-inflammatory 1,4-oxazinone derivatives of the structure:

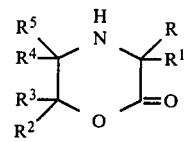

wherein one of R and R$^1$ is hydrogen and the other is —CH$_2$CO$_2$R$^6$ (R$^6$=alkyl) or R and R$^1$ together represent the group =CHCO$_2$R$^6$, R$^2$ and R$^3$ are hydrogen, alkyl, substituted alkyl, phenyl or substituted phenyl or R$^2$ and R$^3$ together represent a single adamantyl group, and R$^4$ and R$^5$ are hydrogen, alkyl, substituted alkyl, phenyl, substituted phenyl, or benzyl, are disclosed herein.

6 Claims, No Drawings

ADAMANTYL CONTAINING 1,4-OXAZINONE DERIVATIVES

FIELD OF THE INVENTION

This invention relates to new 1,4-oxazinone derivatives. More particularly, it relates to derivatives of 3,4,5,6-tetrahydro-1,4-oxazin-2-one. These derivatives, when tested, were found to have antimicrobial activity against *N. gonorrhoeae* or anti-inflammatory activity against carrageenan-induced edema in a laboratory animal model.

STATEMENT OF THE INVENTION

Accordingly, this invention is a 1,4-oxazinone derivative of the formula

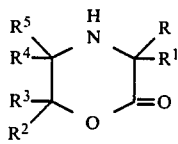

wherein one of R and $R^1$ is hydrogen and the other represents the group $-CH_2CO_2R^6$ or together R and $R^1$ represent the group $=CHCO_2R^6$ where $R^6$ is alkyl, one of $R^2$ and $R^3$ is hydrogen and the other is alkyl, substituted alkyl, phenyl or substituted phenyl or $R^2$ and $R^3$ together represent a single adamantyl group, and $R^4$ and $R^5$ are hydrogen, alkyl, substituted alkyl, phenyl or substituted phenyl, or benzyl.

DETAILED DESCRIPTION OF INVENTION

The compounds of this invention are 3,4,5,6-tetrahydro-1,4-oxazin-2-one derivatives wherein the substituent groups, as shown in the above structural formula, are designated R through $R^5$.

It is preferred that R and $R^1$ represent the group $=CHCO_2R^6$ is a lower alkyl radical ($C_1$-$C_8$) but one of R and $R^1$ may also be hydrogen while the other must then be $-CH_2CO_2R^6$. $R^6$ may have up to 30 carbons, but preferably less than four carbons.

The alkyl radicals of $R^2$ and $R^3$ have up to thirty carbon atoms, preferably up to eight and more preferably less than four carbon atoms. The alkyl portion of the substituted alkyl radicals of $R^2$ and $R^3$ also has up to 30 carbon atoms, but preferably less than four. The substituents of these alkyl radicals are, for example, hydroxy, and alkanoyloxy groups. Alternatively, $R^2$ and $R^3$ together represent a single adamantyl group. In particular, $R^2$ and $R^3$ represent the adamantyl substituent of a compound of the following formula:

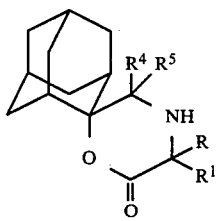

The aromatic radicals which are represented by $R^{2-5}$ are, for example, phenyl and benzyl.

$R^4$ and $R^5$ are preferably hydrogen, alkyl radicals having less than four carbon atoms that may be substituted with a hydroxyl group, or a benzyl group.

The above mentioned alkyl radicals for R through $R^6$ are either straight or branched chained. Examples of these include methyl, ethyl, propyl, isopropyl, isobutyl, butyl, pentyl, isopentyl, hexyl, octyl, isooctyl, decyl, dodecyl, octadecyl, eicosanoyl, tricosanoyl, hexacosanoyl, triacontanoyl and the like. In general, the 1,4-oxazinones of this invention may be prepared by reacting a dialkyl ($C_1$-$C_8$) acetylenedicarboxylate with a compound having both amino and hydroxy substituent groups which will condense with the acetylene compound to form the corresponding 1,4-oxazinone derivative. The aminoalcohol reactant is preferably dissolved in a suitable inert organic solvent, for example, a lower alkanol, ether, alkyl acetate, alkane or mixtures of these. The reaction is usually carried out with reactants employed in equimolar amounts, at ambient temperature and atmospheric pressure but may be run at temperatures ranging from about 15° to 80° C.

EXAMPLES

The following examples are used to show the preparation of representative compounds of this invention.

EXAMPLE 1

3-(Methoxycarbonyl)methylene-spiro[3,4,5,6-tetrahydro-1,4-oxazin-2-one-6,2'-tricyclo[3.3.1.1$^{3,7}$]decane] was prepared as follows: 2-aminomethyl-2-hydroxyadamantane (2.70 g, 0.015 mol) was dissolved in 40 ml of anhydrous ethanol. After stirring for several minutes at room temperature, the solution was treated dropwise with 1.84 ml (0.015 mol) of dimethyl acetylenedicarboxylate. The reaction mixture was stirred at room temperature for 2¼ hours, then the solvent was removed in vacuo to leave 3.3 g (77%) of the desired 1,4-oxazinone derivative. Mp 227°–229° C. (ethanol).

Anal. Calcd. for $C_{16}H_{21}NO_4$: C, 65.96; H, 7.26; N, 4.81. Found: C, 65.80; H, 7.44; N, 4.85.

The above prepared derivative was reduced as follows to form 3-(methoxycarbonyl)methyl-spiro[3,4,5,6-tetrahydro-1,4-oxazin-2-one-6,2'-tricyclo[3.3.1.1$^{3,7}$]decane]. The derivative (13.0 g) was dissolved in acetic acid and hydrogenated in a Parr apparatus over 2.62 g platinum oxide. The hydrogenation was run at room temperature for 2½ hours at pressure that did not exceed 1 atm. After workup and recrystallization from methanol, 8.80 g of the pure 3-(methoxycarbonyl)methyl analog was obtained. Mp 103°–107° C.

Anal. Calcd. for $C_{16}H_{23}NO_4$: C, 65.51; H, 7.90; N, 4.77. Found: C, 64.55; H, 7.53; N, 4.72.

EXAMPLE 2

5,5-Dimethyl-3-(methoxycarbonyl)methylene-3,4,5,6-tetrahydro-1,4-oxazine-2-one was prepared as follows: 2-amino-2-methyl-1-propanol (5.35 ml, 0.056 mol) was dissolved in 100 ml of anhydrous ethanol. Dimethyl acetylenedicarboxylate (7.20 ml, 0.056 mol) was added dropwise at a rate which caused the solution to mildly reflux. Then, the reaction mixture was stirred at ambient temperature for 2 hours, and the solvent was evaporated to yield the desired 1,4-oxazinone derivative. After recrystallization from ethanol, 5.79 g of pure product was obtained melting at 94°–97° C.

Anal. Calcd. for $C_9H_{13}NO_4$: C, 54.26; H, 6.58; N, 7.03. Found: C, 54.42; H, 6.39; N, 6.96.

EXAMPLES 3–12

The following analogs of the 1,4-oxazinone derivative of Example 2 were prepared in a manner similar to the procedure used in Example 2. By reacting dimethyl acetylenedicarboxylate with 2-hydroxypropylamine, 2-amino-1-ethanol, 3-amino-2-hydroxy-1-propanol, 2-amino-1-phenyl-1-propanol, 2-amino-1-phenyl-1-ethanol, 2-amino-2-hydroxymethyl-1-propanol, 2-amino-3-phenyl-1-propanol, 2-amino-1-butanol, and 2-amino-3-methyl-1-butanol, in place of 2-amino-2-methyl-1-propanol of Example 2 the following compounds of Examples 3–12 were prepared:

EXAMPLE 3

6-methyl-3-(methoxycarbonyl)methylene-3,4,5,6-tetrahydro-1,4-oxazin-2-one. The recrystallization solvent was ethanol and the melting point was 98°–101° C.

Anal. Calcd. for $C_8H_{11}NO_4$: C, 51.89; H, 5.99; N, 7.56. Found: C, 51.86; H, 5.99; N, 7.56.

EXAMPLE 4

3-(methoxycarbonyl)methylene-3,4,5,6-tetrahydro-1,4-oxazin-2-one. The recrystallization solvent was ethanol and the melting point was 76°–79° C.

Anal. Calcd. for $C_7H_9NO_4$: C, 49.12; H, 5.30; N, 8.18. Found: C, 48.76; H, 5.32; N, 8.04.

EXAMPLE 5

6-hydroxymethyl-3-(methoxycarbonyl)methylene-3,4,5,6-tetrahydro-1,4-oxazin-2one. The recrystallization solvent was ethanol and the melting point was 112°–114° C.

Anal. Calcd. for $C_8H_{11}NO_5$: C, 47.76; H, 5.51; N, 6.96. Found: C, 47.93; H, 5.55; N, 6.95.

EXAMPLE 6

5-methyl-6-phenyl-(3-methoxycarbonyl)methylene-3,4,5,6-tetrahydro-1,4-oxazin-2-one. The recrystallization solvent was diethyl ether and the melting point was 117° C.

Anal. Calcd. for $C_{14}H_{15}NO_4$: C, 64.36; H, 5.79; N, 5.36. Found: C, 64.29; H, 5.82; N, 5.40.

EXAMPLE 7

6-phenyl-3-(methoxycarbonyl)methylene-3,4,5,6-tetrahydro-1,4-oxazin-2-one. The recrystallization solvent was ethanol and the melting point was 125°–126° C.

Anal. Calcd. for $C_{13}H_{13}NO_4$: C, 63.15; H, 5.30; N, 5.66. Found: C, 63.02; H, 5.44; N, 5.61.

EXAMPLE 8

5-hydroxymethyl-5-methyl-3-(methoxycarbonyl)methylene-3,4,5,6-tetrahydro-1,4-oxazin-2-one. The recrystallization solvent was hexane and the melting point was 62°–63° C.

Anal. Calcd. for $C_9H_{13}NO_5$: C, 50.23; H, 6.09; N, 6.51. Found: C, 50.60; H, 6.30; N, 6.52.

EXAMPLE 9

5-benzyl-3-(methoxycarbonyl)methylene-3,4,5,6-tetrahydro-1,4-oxazin-2-one. The recrystallization solvent was hexane and the melting point was 82°–83° C.

Anal. Calcd. for $C_{14}H_{15}NO_4$: C, 64.36; H, 5.79; N, 5.36. Found: C, 64.56; H, 5.93; N, 5.35.

EXAMPLE 10

5-ethyl-3-(methoxycarbonyl)methylene-3,4,5,6-tetrahydro-1,4-oxazine-2-one. The recrystallization solvent was hexane-ethylacetate (1:1) and the melting point was 68°–70° C.

Anal. Calcd. $C_9H_{13}NO_4$: C, 54.26; H, 6.59; N, 7.03. Found: C, 54.11; H, 6.37; N, 7.04.

EXAMPLE 11

5-isopropyl-3-(methoxycarbonyl)methylene-3,4,5,6-tetrahydro-1,4-oxazin-2-one. This material was a viscous oil.

We claim:

1. A 1,4-oxazinone derivative of the formula

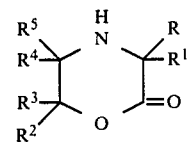

wherein one of R and $R^1$ is hydrogen and the other represents the group $-CH_2CO_2R^6$ or together R and $R^1$ represent the group $=CHCO_2R^6$ where $R^6$ is alkyl, $R^2$ and $R^3$ together represent a single adamantyl group, and $R^4$ and $R^5$ are hydrogen, alkyl, substituted alkyl, phenyl, substituted phenyl, or benzyl.

2. The derivative of claim 1 wherein R and $R^1$ together represent the group $=CHCO_2R^6$ where $R^6$ is a lower alkyl radical.

3. The derivative of claim 2 wherein $R^2$ and $R^3$ together represent a single adamantyl group and $R^4$ and $R^5$ are hydrogen.

4. The derivative of claim 1 wherein one of R and $R^1$ is hydrogen and the other is $-CH_2CO_2R^6$ where $R^6$ is a lower alkyl radical.

5. The derivative of claim 4 wherein $R^2$ and $R^3$ together represent a single adamantyl group, and $R^4$ and $R^5$ are hydrogen.

6. The derivative of claim 4 wherein $R^2$ and $R^3$ are hydrogen, and $R^4$ and $R^5$ are alkyl radicals having less than 4 carbon atoms.

* * * * *